United States Patent
Noda et al.

(10) Patent No.: US 9,480,837 B2
(45) Date of Patent: Nov. 1, 2016

(54) HIGH-FUNCTIONALITY BIOELECTRODE

(71) Applicant: NATIONAL UNIVERSITY CORPORATION NARA INSTITUTE OF SCIENCE AND TECHNOLOGY, Ikoma-shi, Nara (JP)

(72) Inventors: Toshihiko Noda, Ikoma (JP); Takashi Tokuda, Kyoto (JP); Kiyotaka Sasagawa, Kizugawa (JP); Jun Ohta, Souraku-gun (JP)

(73) Assignee: NATIONAL UNIVERSITY CORPORATION NARA INSTITUTE OF SCIENCE AND TECHNOLOGY, Ikoma-shi (JP)

( * ) Notice: Subject to any disclaimer, the term of this patent is extended or adjusted under 35 U.S.C. 154(b) by 0 days.

(21) Appl. No.: 14/763,331

(22) PCT Filed: Feb. 12, 2014

(86) PCT No.: PCT/JP2014/053189
§ 371 (c)(1),
(2) Date: Jul. 24, 2015

(87) PCT Pub. No.: WO2014/126103
PCT Pub. Date: Aug. 21, 2014

(65) Prior Publication Data
US 2015/0367124 A1  Dec. 24, 2015

(30) Foreign Application Priority Data
Feb. 15, 2013  (JP) .................................. 2013-028006

(51) Int. Cl.
*A61N 1/00* (2006.01)
*A61N 1/05* (2006.01)
(Continued)

(52) U.S. Cl.
CPC ........... *A61N 1/0529* (2013.01); *A61B 5/0478* (2013.01); *A61B 5/0492* (2013.01);
(Continued)

(58) Field of Classification Search
CPC .. A61F 9/08; A61N 1/36046; A61N 1/0543; A61N 1/0529; A61B 5/0478
See application file for complete search history.

(56) References Cited

U.S. PATENT DOCUMENTS 3,918,440 A  11/1975  Kraus
6,120,502 A  9/2000  Michelson
(Continued)

FOREIGN PATENT DOCUMENTS

AU  2004211944 A1  8/2004
CA  2511908 A1  8/2004
(Continued)

OTHER PUBLICATIONS

Apr. 1, 2014 International Search Report issued in International Patent Application No. PCT/JP2014/053189.
(Continued)

*Primary Examiner* — Robert N Wieland
(74) *Attorney, Agent, or Firm* — Oliff PLC

(57) ABSTRACT

Providing an electrode structure capable of realizing an electrode array which allows each of the electrodes to be individually controlled while allowing them to be densely arranged and placed in a living body. According to the present invention, an electrode control circuit electrically connected to an electrode body is fixed to a rear portion of the electrode body within a front-viewed contour of the electrode body. This electrode control circuit may be contained in a recess formed in the rear portion of the electrode body, or it may be fixed to the back face of the electrode body. Conversely, an electrically conductive material layer covering the electrode control circuit may be used as the electrode body. A plurality of such bioelectrodes may be arranged in a two-dimensional form on a substrate or connected by a connection line including an electrical wire. Such configurations allow the bioelectrodes to be densely arranged.

15 Claims, 7 Drawing Sheets

(51) Int. Cl.
*A61B 5/0478* (2006.01)
*A61B 5/0492* (2006.01)
*A61B 5/00* (2006.01)

(52) U.S. Cl.
CPC ............ *A61B5/4064* (2013.01); *A61B 5/686* (2013.01); *A61N 1/0531* (2013.01); *A61N 1/0543* (2013.01); *A61B 2562/046* (2013.01)

(56) References Cited

U.S. PATENT DOCUMENTS

| | | | | |
|---|---|---|---|---|
| 9,079,017 | B2* | 7/2015 | Taylor | A61N 1/0526 |
| 2004/0220667 | A1 | 11/2004 | Gelfandbein et al. | |
| 2006/0004431 | A1 | 1/2006 | Fuller et al. | |
| 2009/0210055 | A1* | 8/2009 | Chang | A61F 9/08 623/6.63 |
| 2010/0016928 | A1* | 1/2010 | Zdeblick | A61N 1/05 607/72 |

FOREIGN PATENT DOCUMENTS

| | | |
|---|---|---|
| CA | 2613121 A1 | 1/2007 |
| CN | 1153464 A | 7/1997 |
| DE | 2311817 A1 | 9/1974 |
| EP | 1589916 A2 | 11/2005 |
| FR | 2220231 A1 | 10/1974 |
| GB | 1393703 | 10/1921 |
| JP | S49-120489 A | 11/1974 |
| JP | H10-505248 A | 5/1998 |
| JP | 2004-195206 A | 7/2004 |
| JP | 2006-187409 A | 7/2006 |
| JP | 2006-517136 A | 7/2006 |
| JP | 2007-325652 A | 12/2007 |
| JP | 2009-500084 A | 1/2009 |
| WO | 95/32673 A1 | 12/1995 |
| WO | 2004/071338 A2 | 8/2004 |
| WO | 2007/005842 A2 | 1/2007 |
| WO | 2010/057026 A2 | 5/2010 |

OTHER PUBLICATIONS

Aug. 15, 2015 English Translation of the International Preliminary Report on Patentability issued in International Patent Application No. PCT/JP2014/053189.

Toshihiko Noda et al., "Totsugata shigeki denkyoku to CMOS chippu wo tousai shita furekishiburu jinkou shikaku debaisu no sakusei to kinou jisshou (creation and functional demonstration of flexible artificial vision device equipped with convex stimulating electrodes and CMOS chips);" The 58th Spring Meeting of the Japan Society of Applied Physics and Related Societies 2011 (at Kanagawa Institute of Technology); Mar. 26, 2011.

Jun Ota et al; "Biomedical devices based on semiconductor microelectronics technologies;" The Transactions of the Institute of Electrical Engineers of Japan E (Sensor Micro Machine Bumonshi), Dec. 1, 2011; vol. 131; No. 12; pp. 404 to 407.

Toshihiko Noda et al; "Gankyu ni umekonde momaku o denki shigeki suru handotai gijutsu o oyo shita jinko shikaku device no kaihatsu ni seiko;" The Japan Society of Applied Physics; Mar. 8, 2011.

Feb. 4, 2016 Extended European Search Report issued in European Application No. 14751046.5.

\* cited by examiner

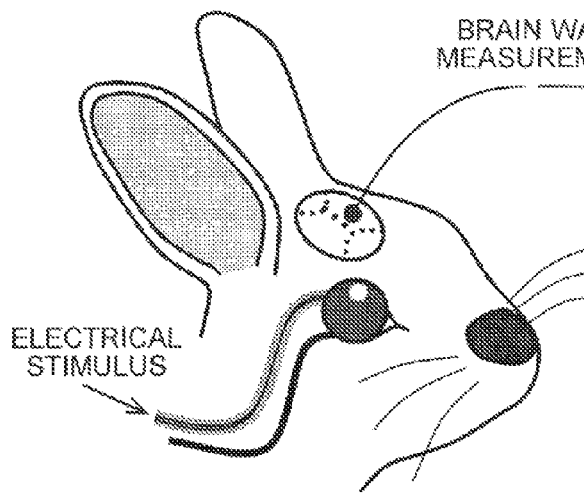
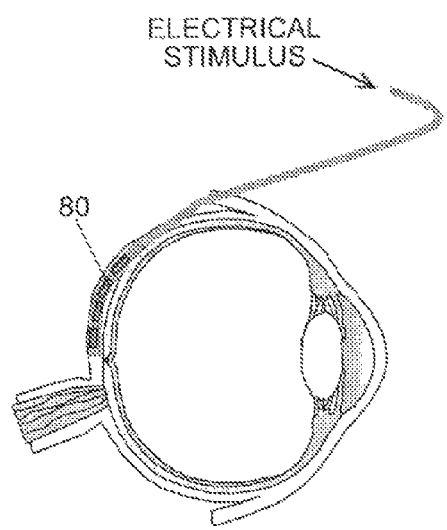
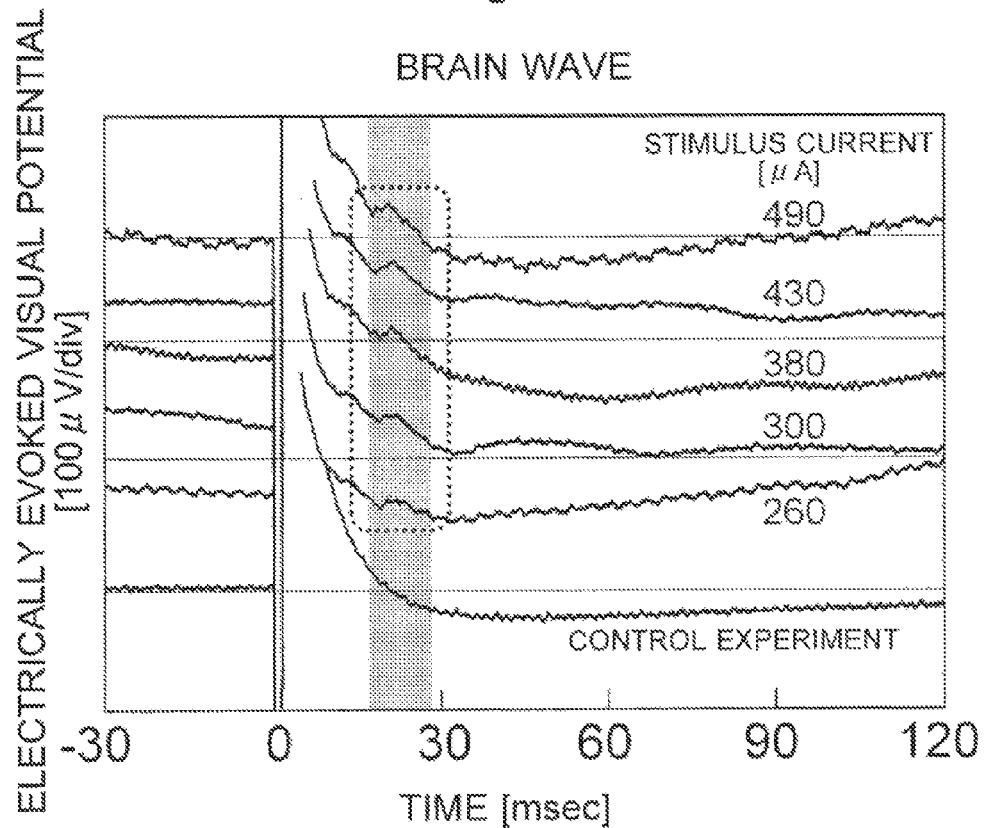

Fig. 14A
Fig. 14B
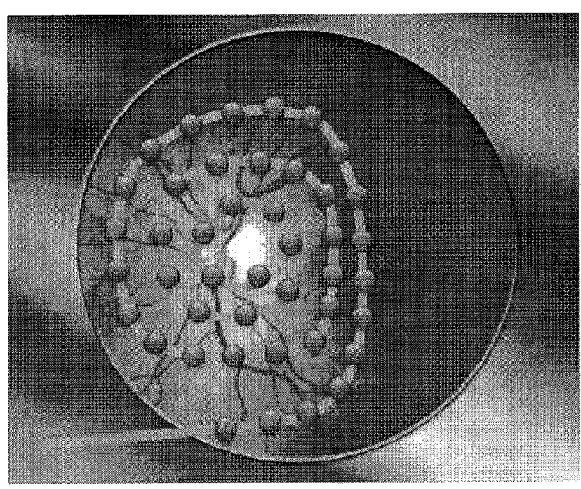
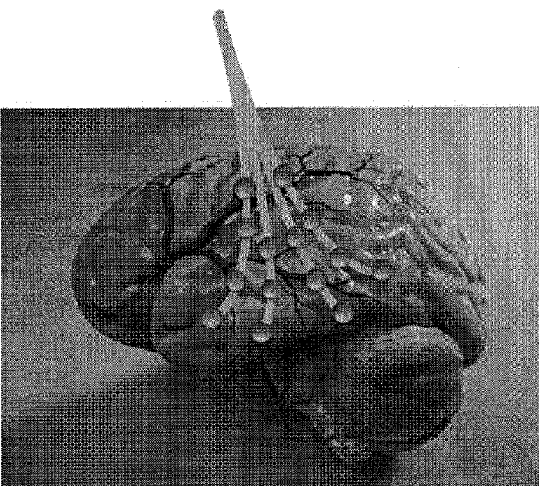

HIGH-FUNCTIONALITY BIOELECTRODE

TECHNICAL FIELD

The present invention relates to a bioelectrode to be attached to a living body (such as an organ of various experimental animals or that of a man) so as to give electrical stimuli to that living body or measure an electric potential, electric current or similar quantity in that living body.

BACKGROUND ART

Electrode arrays having a number of electrodes arranged in various patterns are used as a nerve interface for electrically stimulating a nerve or measuring a nerve action potential. To fulfill this intended purpose, the electrode array should be implanted in a living body and the wires which are bonded to the metallic (e.g. platinum) electrodes should be connected to a stimulator or measurement apparatus. As one method for enabling the multielectrode configuration of the electrode array, the technique of equipping each individual electrode with a small semiconductor chip capable of performing electrode control as well as other functions has been proposed and demonstrated (high-function electrode).

For example, in the case where the sense of sight has been lost due to dysfunction of the visual cells in the retina for converting light into electric signals (examples of the dysfunction include age-related macular degeneration and retinitis pigmentosa), while there is no problem in the ganglion cells in the retina or the optic nerves connecting the retina and the brain, the vision can be virtually restored by taking a visual image of the scene in front of the eyes using a camera or similar device and giving the ganglion cells or other remaining retinal cells two-dimensional electrical stimuli corresponding to that image. Such a system for providing a vision substitution by giving electrical stimuli to the retina is called the "artificial vision device" (for example, see Patent Literature 1).

Non Patent Literature 1 discloses a visual stimulation experiment performed on a rabbit using an artificial vision device employing suprachoroidal transretinal stimulation (STS). The measurement was performed as follows: As shown in FIGS. 1A and 1B, a flexible substrate with an array of 3×3 electrodes arranged as shown in FIG. 3 was planted in an eyeball (sclera) of a rabbit, and electrical stimuli were given to the retina from the choroid side. Meanwhile, electrodes were attached to the visual cortex on the brain of the rabbit, and the electric potential at that point (electrically evoked visual potentials) was measured.

The amount of electric current supplied to the electrodes attached to the eyeball was set at various values and the change in the brain wave was measured, with the point in time of the supply of the electric current (or stimulus) defined as the zero point. Consequently, as shown in FIG. 2, it was confirmed that the peak height (response) of the brain wave increases with an increase in the current value (stimulus). The time delay from the stimulation (approximately 20 msec) was roughly equal to the transmission delay of the vision investigated by another experiment. These facts confirm that this electrode array substrate 80 (in FIG. 3) was correctly acting as an eyeball-stimulating electrode.

CITATION LIST

Patent Literature

Patent Literature 1: JP 2006-187409 A

Non Patent Literature

Non Patent Literature 1: Toshihiko Noda et al., "Totsugata Shigeki Denkyoku To CMOS Chippu Wo Tousai Shita Furekishiburu Jinkou Shikaku Debaisu No Sakusei To Kinou Jisshou (Creation and Functional Demonstration of Flexible Artificial Vision Device Equipped with Convex Stimulating Electrodes and CMOS Chips)", Mar. 26, 2011, The 58$^{th}$ Spring Meeting of the Japan Society of Applied Physics and Related Societies 2011 (at Kanagawa Institute of Technology)

SUMMARY OF INVENTION

Technical Problem

As shown in FIG. 3, the electrode array substrate 80 described in Non Patent Literature 1 has an electrode control circuit chip 82 for each electrode 81 to control the amount and timing of the electric current or voltage supplied to the electrode 81 as well as other parameters. This configuration requires only four wires (for positive and negative power sources as well as first and second operation control lines) to be connected to the entire substrate regardless of the number of electrodes 81, thus allowing a considerable number of electrodes 81 to be embedded in a living body (e.g. an eyeball).

The electrode control circuit chip 82 for controlling each electrode 81 is small in size. However, the spacing of the electrodes 81 cannot be small since the chip space must be provided for each individual electrode 81 as shown in FIG. 4. Therefore, in particular, it is difficult to densely arrange the electrodes 81 in a small part (e.g. eyeball) of the living body.

The present invention has been developed in view of the previously described problem. Its primary objective is to provide an electrode structure capable of realizing an electrode array which allows each of the electrodes to be individually controlled while allowing them to be densely arranged and placed in a living body.

Solution to Problem

A bioelectrode according to the present invention developed for achieving the aforementioned objective is characterized in that an electrode control circuit electrically connected to an electrode body is fixed to a rear portion of the electrode body within a front-viewed contour of the electrode body.

The phrase "within a front-viewed contour of the electrode body" means that the portion concerned lies within the contour of the electrode body when the electrode body is viewed from the side that is to be in contact with, pushed onto or stuck into a living body (the front side of the electrode body).

Specifically, the electrode control circuit may be contained in a recess formed in the rear portion of the electrode body. It is also possible to fix the circuit to the back face (rear face) of the electrode body, without forming any recess in the rear portion of the electrode body. Furthermore, as opposed to forming a recess in a solid electrode body and containing the circuit in that recess, the electrode control circuit may be covered with an electrically conductive layer and use this layer as the electrode body.

These bioelectrodes may be singly used. Alternatively, they can be arranged in a two-dimensional form (array) on a substrate and used as an electrode array, or be connected by a connection line including an electrical wire and used as a connection-type bioelectrode.

Advantageous Effects of the Invention

In the bioelectrode according to the present invention, since the control circuit for controlling the electrode body is fixed to the rear portion of the electrode body within the front-viewed contour of the electrode body, the electrode body can be implanted in a compact area of a living body without additionally providing a lateral space for the electrode control circuit. This is particularly advantageous when many electrode bodies need to be implanted in a living body, since the electrode bodies can be densely arranged so as to give stimuli to the living body or measure biopotential or other quantities at a higher level of planer (or linear) density.

By forming a recess in the rear portion of the electrode body and containing the electrode control circuit in that recess, the entire length of the bioelectrode inclusive of the electrode body and the electrode control circuit can be reduced. In the case of implanting this bioelectrode in a living body, a liquid-tight separation between the electrode control circuit and the living body can be achieved by simply sealing the open side of the recess. Therefore, it is easy to prevent both the invasion on the living body by the electrode control circuit and the invasion of biological solutions into the electrode control circuit.

BRIEF DESCRIPTION OF DRAWINGS

FIGS. 1A and 1B are illustrations showing the setup of a visual stimulation experiment performed on a rabbit using an artificial vision device.

FIG. 2 is a graph showing the magnitude of the stimulus and the change in the brain wave, which is a result of the aforementioned visual stimulation experiment performed on the rabbit.

FIG. 12A is a bioelectrode with the control circuit fixed to the rear face, FIG. 12B is a bioelectrode with the control circuit encapsulated, and FIG. 12C is a bioelectrode coated with an electrically conductive resin or ceramic encapsulation material.

FIGS. 14A and 14B are model views showing application examples of the connection-type bioelectrode, where FIG. 14A shows an application to an eyeball and FIG. 14B shows an application to a brain.

DESCRIPTION OF EMBODIMENTS

Figure 3:
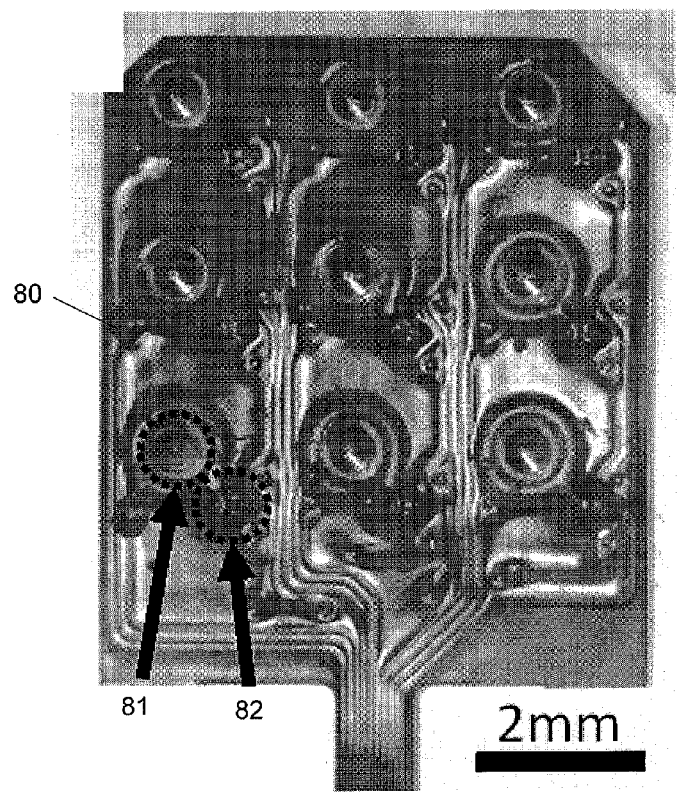
FIG. 3 is a plan view of the electrode array substrate used in the aforementioned visual stimulation experiment performed on the rabbit.
Figure 4:
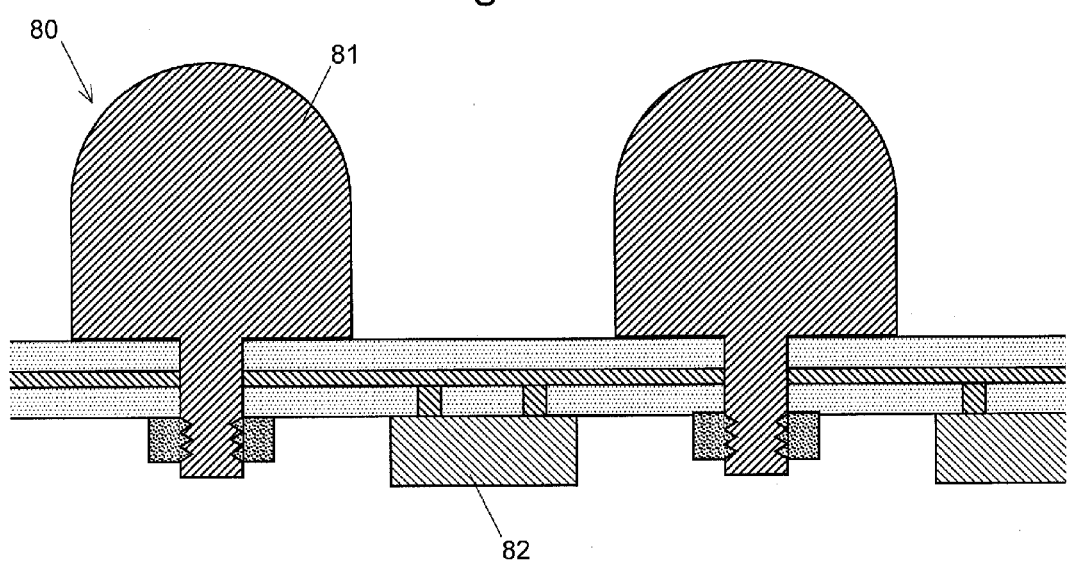
FIG. 4 is a sectional view showing the structure of the electrode array substrate used in the aforementioned visual stimulation experiment performed on the rabbit.
Figure 5A:
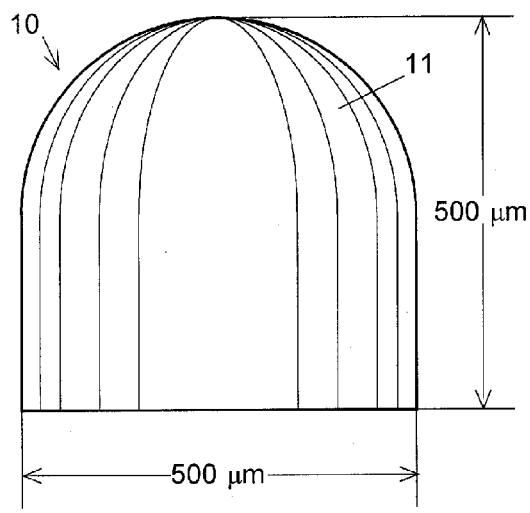
FIGS. 5A-5C are a side view, sectional view and bottom view, respectively, of a bullet-shaped electrode body used in an artificial vision device as one embodiment of the bioelectrode according to the present invention.
Figure 5B:
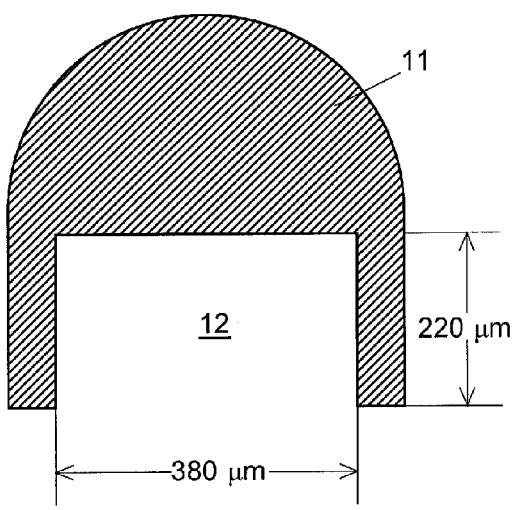
Figure 5C:
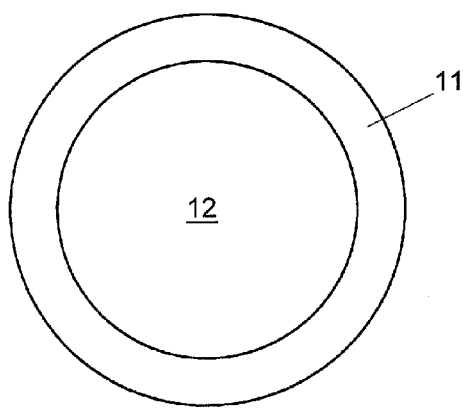

An artificial vision device as one embodiment of the bioelectrode according to the present invention is hereinafter described. As shown in FIGS. 5A-5C, the bioelectrode 10 used in the artificial vision device of the present embodiment uses a bullet-shaped electrode body 11. The electrode body 11 may be made of any material compatible with living bodies. Examples of the available materials include: metallic materials, such as platinum (Pt), gold (Au), titanium (Ti) or an alloy of these kinds of metal; electrically conductive compounds, such as iridium oxide (IrOx) or titanium nitride (TiN); and electrically conductive polymers, such as poly (3,4-ethylenedioxythiophene) or PEDOT. Naturally, it is also possible to use such electrically conductive materials for the surface coating while creating the inner part of the electrode body from resin, ceramic or other non-conductive materials. In the case of using an inner part made of a resin, ceramic or similar non-conductive material, it is necessary to form an electrical channel between the electrode control circuit chip and the electrically conductive coating on the surface (as will be described later). Compared to resin, using a metallic or ceramic material allows the electrode control circuit chip to be encapsulated for a longer period of time within a hermetic space surrounded by the metallic or ceramic material. Accordingly, it is preferable to use a metallic material for the electrode body 11 or create the inner part of the electrode body 11 from ceramic. In this case, the electrode body 11 can double as the encapsulation material (which will be described later). Although the following descriptions deal with the case of a bullet-shaped electrode body 11 with a size of 500 μm, the present invention is not limited to this size but may have any size that allows the electrode body to be implanted in a living body, e.g. from 10 μm to 500 μm. The "size" of the electrode body 11 in the present context means the depth, width or height of the electrode body 11, whichever is the largest.

As shown in FIGS. 5B and 5C, the electrode body 11 of the present embodiment has, in its rear portion, a recess 12 for containing an electrode control circuit chip 20.

Figure 6:
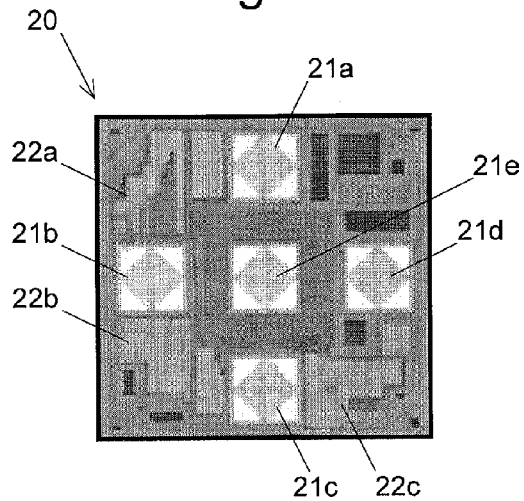
FIG. 6 is a plan view of an electrode control circuit chip used in the artificial vision device of the aforementioned embodiment.

The electrode control circuit chip 20 is a single chip on which a circuit for controlling electric current and/or voltage supplied to the electrode body 11 is created. As shown in FIG. 6, it includes five electrode pads 21a-21e and three control circuits (or similar elements) 22a-22c arranged among those pads. The electrode pads 21c and 21d are the terminals for receiving positive and negative DC power from an external source, while the electrode pads 21a and 21b are the terminals for receiving externally-supplied operation control signals. As will be described later, these four electrode pads 21a-21d are individually and respectively connected to the four electrical wires provided in a substrate 31. Based on the operation control signals thus supplied from an external control circuit, the electrode control circuit chip 20 performs various mathematical operations and appropriately controls the electric current and/or voltage supplied from the positive and negative power sources so that a controlled amount of current and/or voltage will be fed to the central electrode pad 21e. The electric current and/or voltage fed to the electrode pad 21e is supplied to the electrode body 11 through a wire provided in the substrate 31.

This electrode control circuit chip 20 is contained in the recess 12 in the rear portion of the electrode body 11 and fixed by filling the surrounding space with a resin or similar material. In other words, the electrode control circuit chip 20 is encapsulated in the recess 12 in the rear portion of the electrode body 11 with a resin or similar encapsulation material. A resin, metallic or ceramic material can be used as the encapsulation material. Compared to resin, using a metallic or ceramic material allows the electrode control circuit chip to be encapsulated for a longer period of time within an hermetic space surrounded by the metallic or ceramic material. Therefore, they can be suitably used as the encapsulation material for implantation in a living body. When the electrode control circuit chip 20 is inserted into the electrode body 11, these two components should be oriented in a specified way, and furthermore, a mark should be put on the outside of the electrode body 11 so that one can locate the position of the contained electrode control circuit chip 20 around the axis.

Figure 7:
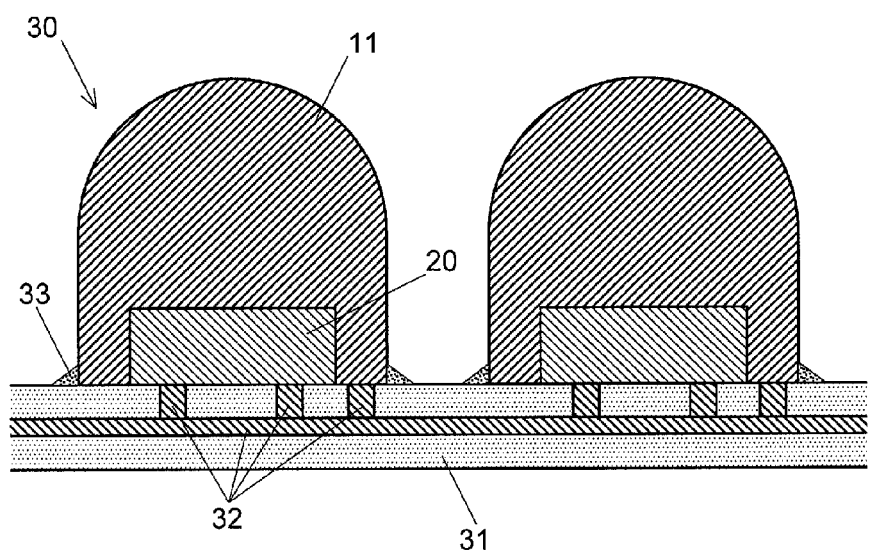
FIG. 7 is a sectional view showing the structure of an electrode array substrate used in the artificial vision device of the aforementioned embodiment.
Figure 8:
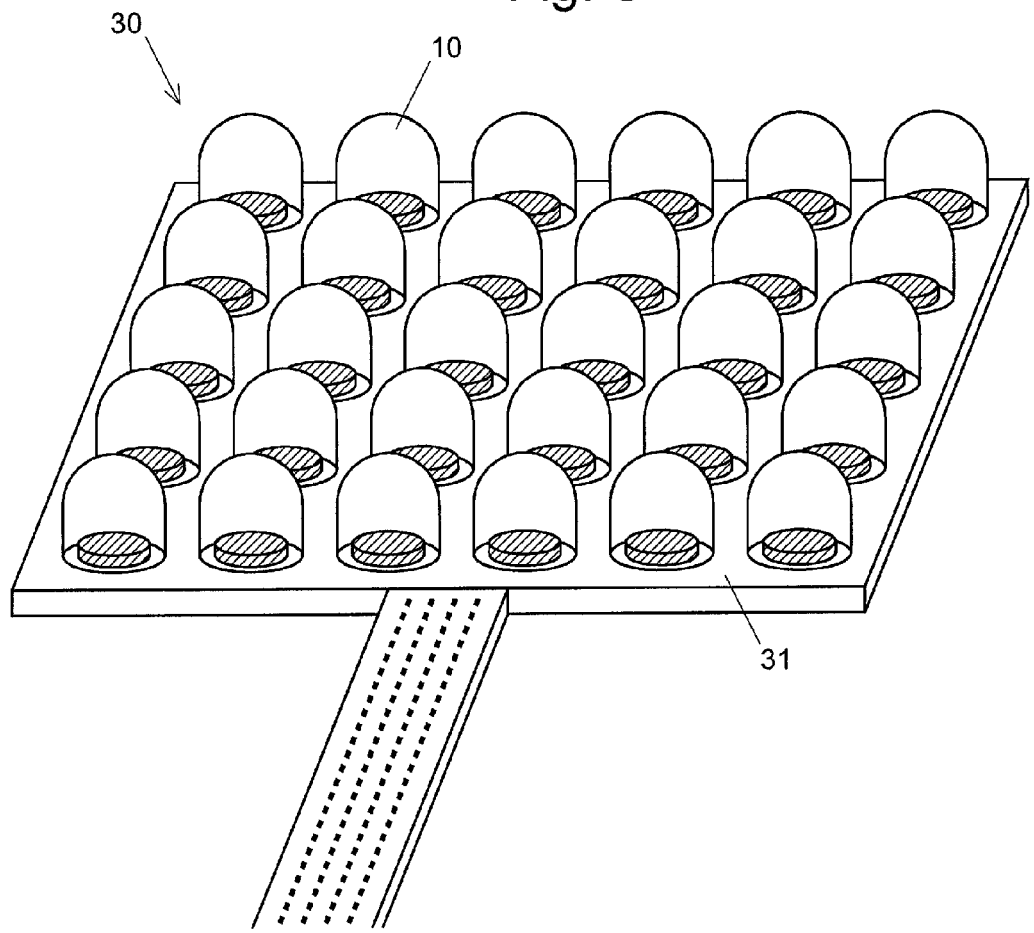
FIG. 8 is a perspective view of the electrode array substrate used in the artificial vision device of the aforementioned embodiment.

As shown in FIG. 8, a plurality of electrode bodies 11 (bioelectrodes 10) each of which has the electrode control circuit chip 20 contained in the recess 12 in its rear portion are two-dimensionally arranged on and fixed to a flexible substrate 31. In this process, each electrode body 11 should be placed at a specific position and in a specific direction with respect to the substrate 31 so that the electrode pads 21a-21e of the electrode control circuit chip 20 will be correctly brought into electrical connection with the counterpart electrode pads on the substrate 31. As a result, as shown in FIG. 7, the wires 32 provided in the substrate 31 are connected to the electrode pads 21a-21e of the electrode control circuit chip 20, allowing the operation control signals and power from external sources to be correctly supplied to each electrode control circuit chip 20. The region surrounding the bottom portion of the electrode body 11 placed on the substrate 31 is sealed with a sealant 33.

As shown in FIG. 8, the electrode array substrate 30 thus created as one example of the bioelectrode substrate has the bioelectrodes 10 densely arranged without the electrode control circuit chips 20 placed in between. Therefore, it is possible to give precise electrical stimuli to target sites of the living body. Since the electrode control circuit chip 20 is contained in the recess 12 of each electrode body 11 and sealed on the flexible substrate 31 with the sealant 33, the various component substances in the electrode control circuit chip 20 will not penetrate into the living body. Thus, the living body is safely protected and can be correctly tested without being influenced by those substances. Conversely, biological solutions are prevented from invading into the electrode control circuit chip 20 and corroding the electric circuits or obstructing electrical conductions. Such characteristics of the bioelectrode 10 are important since, in some cases, the implanted bioelectrode 10 needs to be left in the living body for a number of years.

Figure 9:
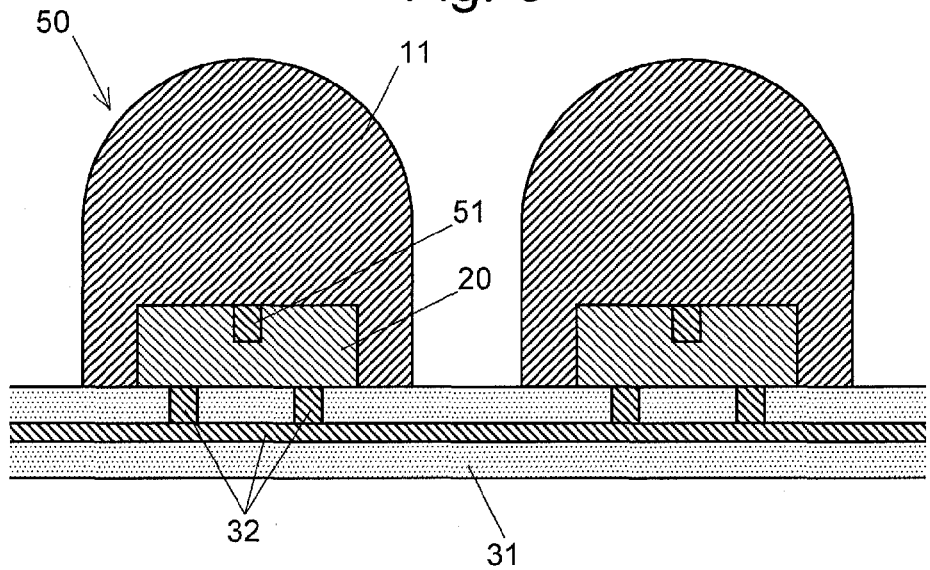
FIG. 9 is a sectional view showing the structure of an electrode array substrate using an electrode body as another embodiment of the present invention.

Another example of the bioelectrode according to the present invention is shown in FIG. 9. This bioelectrode 50 is similar to the previous embodiment in that the electrode control circuit chip 20 is contained in the recess in the rear portion of the electrode body 11. The characteristic point is that the supply of the electric current and/or voltage from the electrode control circuit chip 20 to the electrode body 11 is directly performed from an electrode pad 51 provided in the upper portion (on the side closer to the tip of the electrode body 11) of the electrode control circuit chip 20 to the electrode body 11. This configuration simplifies the pattern of the conductor wires in the substrate 31.

Figure 10:
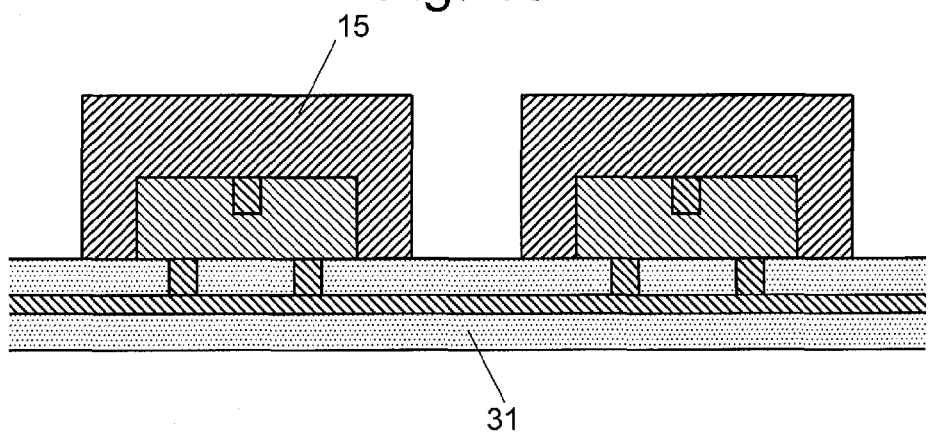
FIG. 10 is a sectional view showing the structure of an electrode array substrate using a plate-shaped electrode body as another embodiment of the present invention.

In any of the previously described examples, the electrode body 11 is bullet shaped. However, as shown in FIG. 10, the electrode body 15 may be shaped like a plate having a circular or rectangular form (or any other form).

Figure 11:
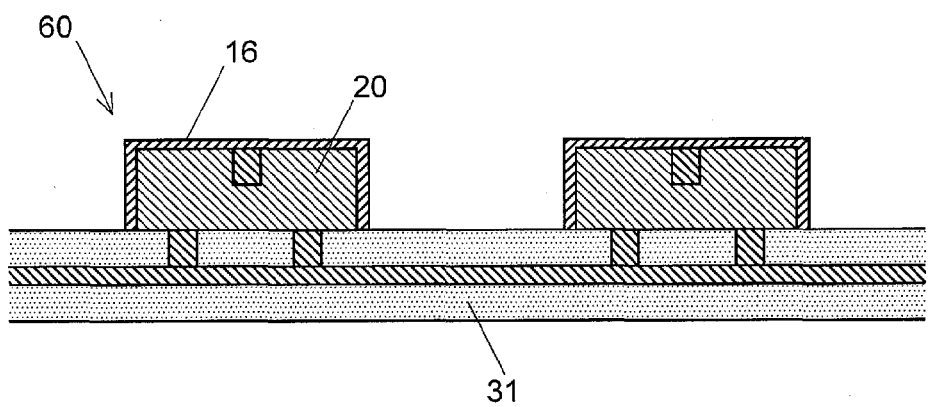
FIG. 11 is a sectional view showing the structure of an electrode array substrate using a coating electrode body as another embodiment of the present invention.

Furthermore, as opposed to those examples in which a solid body of an electrically conductive material is used as the electrode body and the electrode control circuit chip is contained in the recess formed in that body, a bioelectrode 60 as shown in FIG. 11 may be constructed by covering the electrode control circuit chip 20 with an electrically conductive material layer 16 formed by application, plating or similar processes.

Figure 12A:
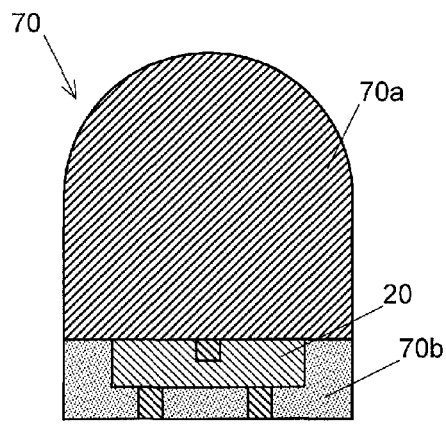
FIGS. 12A-12C are sectional views of other embodiments of the present inventions, where
Figure 12B:
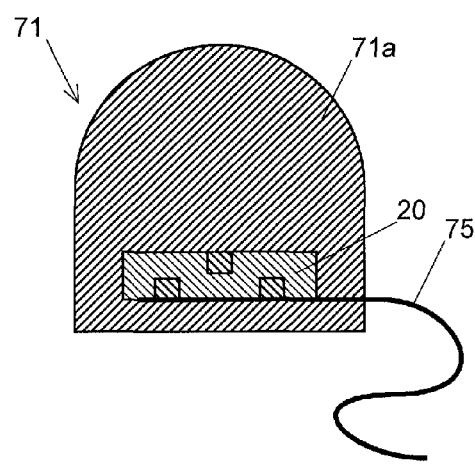
Figure 12C:
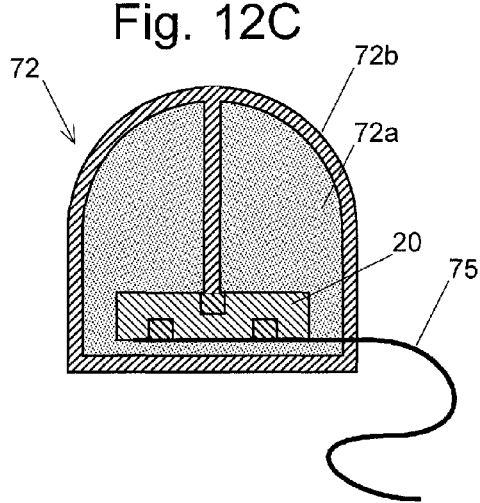
Figure 13:
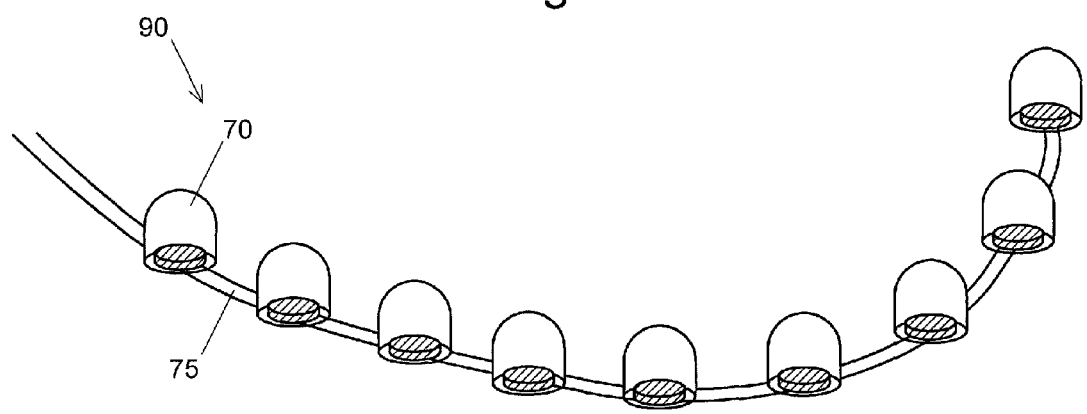
FIG. 13 is a perspective view of a connection-type bioelectrode consisting of the bioelectrodes connected by a connection line including a conductor wire.

Furthermore, as shown in FIG. 12A, it is possible to fix the electrode control circuit chip 20 to the rear portion of the electrode body 70a instead of containing it in the electrode body. In this case, the electrode control circuit chip 20 is fixed to the electrode body 70a by attaching it to the electrode body 70a with its electrode pads electrically in contact with the rear portion of the electrode body 70a, and subsequently covering it with a resin material 70b or the like and curing the material. In other words, the electrode control circuit chip 20 is encapsulated on the rear portion of the electrode body 70a with the resin material 70b as the encapsulation material. This bioelectrode 70 is not fixed to the substrate 31 as in the previous embodiments, and therefore, can be singly used. For example, as shown in FIG. 13, it is possible to create, as one example of the bioelectrode connection line, a connection-type bioelectrode 90 having a plurality of bioelectrodes 70 connected by a connection line 75. Connecting the bioelectrodes 70 by the connection line 75 including a conductor wire allows the bioelectrodes 70 to be arbitrarily arranged at desired sites of a living body. FIG. 14A shows an example of attaching the electrodes to the fundus of the eyeball, while FIG. 14B shows an example of attaching them to the brain. For such an application using the connection line, a bioelectrode 71 as shown in FIG. 12B can also be used, in which the electrode control circuit 20 is encapsulated in the bioelectrode 71 using an electrically conductive material 71a as the encapsulation material (including the case where this is a metallic material). A similar bioelectrode 72 is shown in FIG. 12C, which can be obtained by encapsulating the electrode control circuit 20 with an electrically non-conductive resin, ceramic or similar material 72a as the encapsulation material forming the inner part of the bioelectrode 72, and subsequently coating this part with an electrically conductive material 72b.

REFERENCE SIGNS LIST 10, 50, 60, 70, 71, 72 . . . Bioelectrode
11, 15, 17 . . . Electrode Body
12 . . . Recess
16 . . . Electrically Conductive Material Layer
18 . . . Resin
20 . . . Electrode Control Circuit Chip
21a-21e . . . Electrode Pad
22a-22c . . . Electrode Control Circuit
30 . . . Electrode Array Substrate
31 . . . Substrate
32 . . . Wire in the Substrate
33 . . . Sealant 51 . . . Electrode Pad
75 . . . Connection Line
80 . . . Electrode Array Substrate
81 . . . Electrode
82 . . . Electrode Control Circuit Chip
90 . . . Connection-Type Bioelectrode

The invention claimed is:

1. A bioelectrode substrate, comprising:
a substrate; and
a plurality of bioelectrodes fixed to the substrate, wherein:
each of the plurality of bioelectrodes has a bullet-shaped or plate-shaped electrode body and an electrode control circuit chip electrically connected to the electrode body for controlling electric current and voltage supplied to the electrode body upon receiving an externally-supplied operation signal, and the electrode control circuit chip is fixed to a rear portion of the electrode body within a front-viewed contour of the electrode body.

2. The bioelectrode substrate according to claim 1, wherein the bioelectrode substrate is an optic nerve-stimulating electrode substrate for stimulating an optic nerve through a retina.

3. The bioelectrode substrate according to claim 1, wherein the electrode control circuit chip is contained in a recess formed in the rear portion of the electrode body.

4. The bioelectrode substrate according to claim 1, wherein the electrode control circuit chip is hermetically or liquid-tightly sealed in the rear portion of the electrode body with an encapsulation material.

5. The bioelectrode substrate according to claim 4, wherein the encapsulation material is a resin, metallic or ceramic material.

6. The bioelectrode substrate according to claim 1, wherein the electrode body is made of a metallic material which is platinum, titanium, gold or an alloy of these kinds of metal, or is made of an electrically conductive material which is an electrically conductive compound or an electrically conductive polymer.

7. The bioelectrode substrate according to claim 1, wherein each of the plurality of bioelectrodes has a size within a range from 10 µm to 500 µm, where the size is defined as a depth, width or height of the bioelectrode, whichever is a largest.

8. A bioelectrode connection line, comprising:
a connection line including an electrical wire; and
a plurality of bioelectrodes connected by the connection line, wherein:
each of the plurality of bioelectrodes has a bullet-shaped or plate-shaped electrode body and an electrode control circuit chip electrically connected to the electrode body for controlling electric current and voltage supplied to the electrode body upon receiving an externally-supplied operation signal, and the electrode control circuit chip is fixed to a rear portion of the electrode body within a front-viewed contour of the electrode body.

9. The bioelectrode connection line according to claim 8, wherein the bioelectrode connection line is an optic nerve-stimulating electrode connection line for stimulating an optic nerve through a retina.

10. The bioelectrode connection line according to claim 8, wherein the bioelectrode connection line is a brain-stimulating electrode connection line for stimulating a brain.

11. The bioelectrode connection line according to claim 8, wherein the electrode control circuit chip is contained in a recess formed in the rear portion of the electrode body.

12. The bioelectrode connection line according to claim 8, wherein the electrode control circuit chip is hermetically or liquid-tightly sealed in the rear portion of the electrode body with an encapsulation material.

13. The bioelectrode connection line according to claim 12, wherein the encapsulation material is a resin, metallic or ceramic material.

14. The bioelectrode connection line according to claim 8, wherein the electrode body is made of a metallic material which is platinum, titanium, gold or an alloy of these kinds of metal, or is made of an electrically conductive material which is an electrically conductive compound or an electrically conductive polymer.

15. The bioelectrode connection line according to claim 8, wherein each of the plurality of bioelectrodes has a size within a range from 10 µm to 500 µm, where the size is defined as a depth, width or height of the bioelectrode, whichever is a largest.

* * * * *